United States Patent [19]
Holub et al.

[11] Patent Number: 6,084,136
[45] Date of Patent: Jul. 4, 2000

[54] PROCESS FOR THE PREPARATION OF TETRABROMOBISPHENOL-A

[75] Inventors: Richard A. Holub, Baton Rouge, La.; Steven R. Alferi, Friendswood, Tex.; Bonnie G. McKinnie, Hegenheim, France; Hassan Y. Elnagar, Baton Rouge, La.

[73] Assignee: Albmarle Corporation, Richmond, Va.

[21] Appl. No.: 09/096,332

[22] Filed: Jun. 11, 1998

Related U.S. Application Data

[63] Continuation-in-part of application No. 08/550,044, Oct. 30, 1995, Pat. No. 5,723,690, application No. 08/426,996, Apr. 24, 1995, abandoned, and application No. 08/945,158, Oct. 21, 1997, which is a continuation-in-part of application No. 08/426,998, Apr. 24, 1995, abandoned, which is a continuation-in-part of application No. 08/398,837, Mar. 6, 1995, abandoned, which is a continuation of application No. 08/426,997, Apr. 24, 1995, Pat. No. 5,527,971.

[51] Int. Cl.$^7$ .................................................. C07C 37/68
[52] U.S. Cl. ...................... 568/725; 568/722; 568/723; 568/727; 568/779; 568/776; 568/726
[58] Field of Search .................................... 568/721, 722, 568/723, 725, 726, 727, 776, 779

[56] References Cited

U.S. PATENT DOCUMENTS

| | | | |
|---|---|---|---|
| 2,455,652 | 12/1948 | Bralley et al. ........................ | 260/77.5 |
| 3,029,291 | 4/1962 | Dietzler .................................. | 260/619 |
| 3,143,575 | 8/1964 | Bryner et al. .......................... | 260/619 |
| 3,182,088 | 5/1965 | Hennis ................................... | 260/619 |
| 3,234,289 | 2/1966 | Hennis ................................... | 260/619 |
| 3,363,007 | 1/1968 | Majewski et al. ..................... | 260/619 |
| 3,546,302 | 12/1970 | Asadorian et al. .................... | 260/619 |
| 3,868,423 | 2/1975 | Montanari et al. ................. | 260/619 A |
| 3,929,907 | 12/1975 | Janzon et al. ....................... | 260/619 R |
| 4,013,728 | 3/1977 | Brackenridge ..................... | 260/619 A |
| 4,036,894 | 7/1977 | Jenkner .............................. | 260/619 A |
| 4,112,242 | 9/1978 | Swietoslawski et al. .............. | 568/726 |
| 4,180,684 | 12/1979 | Kleinschmit et al. .................. | 568/726 |
| 4,282,391 | 8/1981 | Quinn et al. ........................... | 568/726 |
| 4,283,566 | 8/1981 | Mark ...................................... | 568/726 |
| 4,291,177 | 9/1981 | Mark et al. ............................. | 568/726 |
| 4,302,614 | 11/1981 | Dannenberg et al. ................. | 568/641 |
| 4,451,675 | 5/1984 | Bounds ................................. | 568/726 |
| 4,628,124 | 12/1986 | McKinnie et al. ..................... | 568/726 |
| 4,692,555 | 9/1987 | Shin ....................................... | 568/772 |
| 4,701,568 | 10/1987 | McKinnie et al. ..................... | 568/726 |
| 4,783,556 | 11/1988 | Mitchell et al. ....................... | 568/726 |
| 4,909,997 | 3/1990 | Mitchell et al. ....................... | 422/225 |
| 4,990,321 | 2/1991 | Sato et al. .............................. | 423/486 |
| 5,008,469 | 4/1991 | Eguchi et al. ......................... | 568/722 |
| 5,017,728 | 5/1991 | McKinnie et al. ..................... | 568/726 |
| 5,059,722 | 10/1991 | Mitchell et al. ....................... | 568/226 |
| 5,059,726 | 10/1991 | Eguchi et al. ......................... | 568/726 |
| 5,068,463 | 11/1991 | Walter ................................... | 568/726 |
| 5,107,035 | 4/1992 | Hines et al. ........................... | 568/726 |
| 5,138,103 | 8/1992 | Eguchi et al. ......................... | 568/726 |
| 5,208,389 | 5/1993 | McKinnie et al. ..................... | 568/726 |
| 5,237,112 | 8/1993 | LaRose .................................. | 568/726 |
| 5,283,375 | 2/1994 | McKinnie et al. ..................... | 568/726 |
| 5,302,761 | 4/1994 | Tamabayashi et al. ................ | 568/726 |
| 5,446,212 | 8/1995 | Sanders et al. ........................ | 568/726 |
| 5,527,971 | 6/1996 | McKinnie .............................. | 568/726 |
| 5,723,690 | 3/1998 | McKinnie .............................. | 568/726 |
| 5,847,232 | 12/1998 | McKinnie .............................. | 568/726 |

FOREIGN PATENT DOCUMENTS

| | | | |
|---|---|---|---|
| 686772 | 5/1964 | Canada ................................. | 260/620 |
| 706433 | 3/1965 | Canada ................................. | 260/620 |
| 0367869 | 5/1990 | European Pat. Off. . | |
| 0380363 | 8/1990 | European Pat. Off. . | |
| 0380365 | 8/1990 | European Pat. Off. . | |
| 0472395 | 2/1992 | European Pat. Off. . | |
| 0572154 | 12/1993 | European Pat. Off. . | |
| 0574031 | 12/1993 | European Pat. Off. . | |
| 2274586 | 1/1976 | France . | |
| 2041220 | 3/1971 | Germany . | |
| 3417027 | 11/1985 | Germany . | |
| 64410 | 11/1981 | Israel . | |
| 225034 | 12/1983 | Japan . | |
| 58728 | 12/1985 | Japan . | |
| 48641 | 3/1987 | Japan . | |
| 316748 | 12/1988 | Japan . | |
| 196747 | 8/1990 | Japan . | |
| 4099743 | 3/1992 | Japan . | |
| 5213804 | 8/1993 | Japan . | |
| 5229976 | 9/1993 | Japan . | |
| 379054 | 12/1993 | Japan . | |
| 2026280 | 1/1995 | Russian Federation . | |
| 949306 | 2/1964 | United Kingdom . | |
| 1031500 | 6/1966 | United Kingdom . | |
| 1316415 | 5/1973 | United Kingdom . | |
| 9611227 | 4/1996 | WIPO . | |
| 9620911 | 7/1996 | WIPO . | |

OTHER PUBLICATIONS

Chemical Abstract No. 78(1):3946j—*Chemical Abstracts*, vol. 78, 1973, p. 328.

Chemical Abstract No. 86(25):189500c—*Chemical Abstracts*, vol. 86, 1977, p. 570.

Chemical Abstract No. 96(19):162322r—*Chemical Abstracts*, vol. 96, 1982, p. 718.

Chemical Abstract No. 104(17):148492y—*Chemical Abstracts*, vol. 104, 1986, p. 656.

(List continued on next page.)

*Primary Examiner*—Shailendra Kumar
*Assistant Examiner*—Sreeni Padmanabhan
*Attorney, Agent, or Firm*—E. E. Spielman, Jr.

[57] ABSTRACT

This invention relates to a process for the production of tetrabromobisphenol-A by the bromination of bisphenol-A, which process features: (a) feeding to a reaction mass (i) bisphenol-A and (ii) a stream of gaseous bromine, the gaseous stream having a Reynold's No. $\geq 40,000$; (b) the reaction mass containing from about 50 to about 20,000 ppm unreacted bromine and less than 20 wt % HBr; and (c) the reaction mass having precipitated therefrom tetrabromobisphenol-A, all of (a)(ii), (b) and (c) occurring during the bisphenol-A feed.

25 Claims, 1 Drawing Sheet

OTHER PUBLICATIONS

Chemical Abstract No. 104(23):206899z—*Chemical Abstracts*, vol. 104, 1986, p. 716.

Islam et al., "Tetrahalogenated 4:4'–Dihydroxydiphen;ylalkanes, their Synthesis and some of their Reactions," *Egypt. J. Chem.* 20, No. 5, pp. 483–490 (1977).

Sadygov, et al., "Oxidative bromination of 2,2–bis(4'–hydroxyphenyl)propane," Institute of Organochlorine Synthesis, Academy of Sciences of the Azerbaidzhan SSR, Sumgait, U.S.S.R., 1990, pp. 109–112 (Translation attached—pp. 1–7).

Levenspiel, Chemical Reaction Eng., (1962), p. 126.

FIG. I
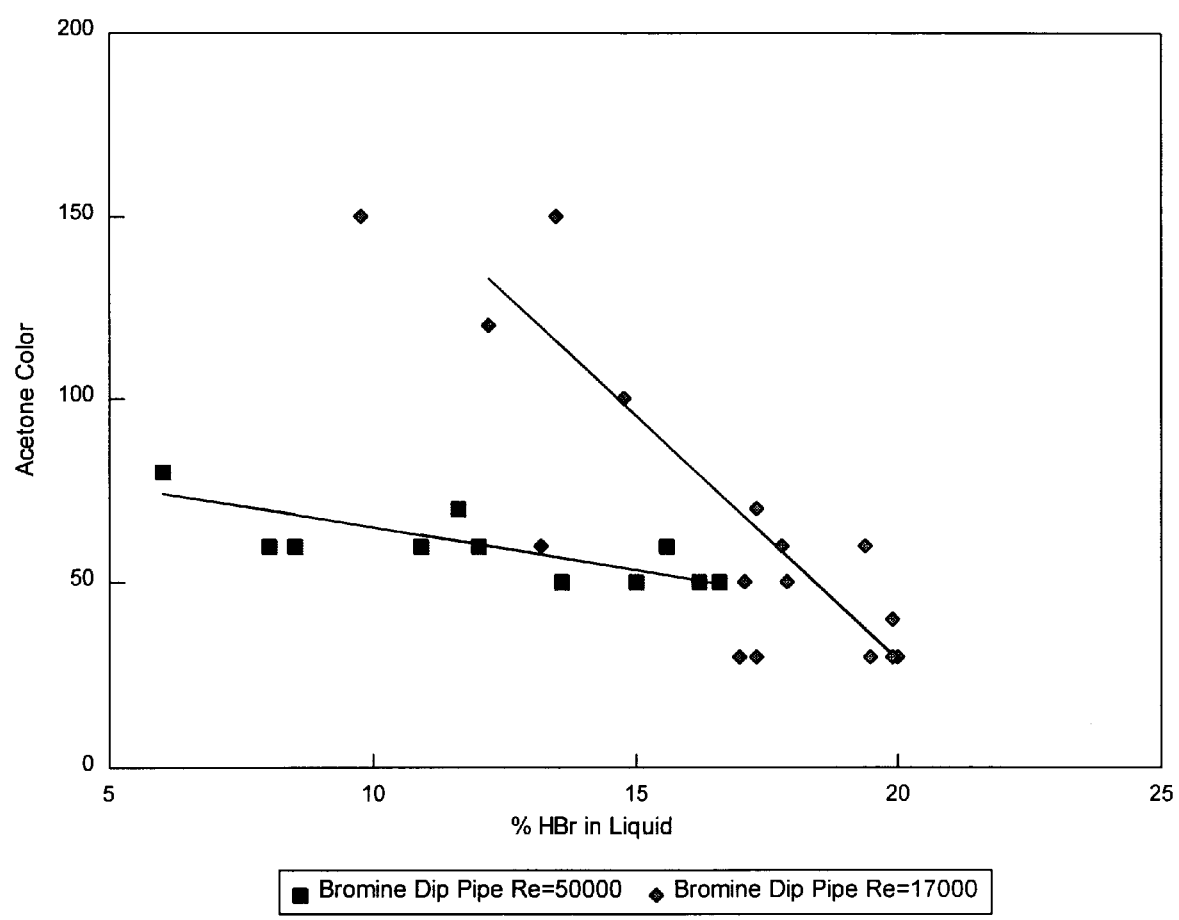

PROCESS FOR THE PREPARATION OF TETRABROMOBISPHENOL-A

This application is a continuation-in-part of U.S. Ser. No. 08/945,158 filed Oct. 21, 1997, which is (1) a continuation-in-part of U.S. Ser. No. 08/426,998 filed Apr. 24, 1995, now abandoned, which, in turn, is a continuation-in-part of U.S. Ser. No. 08/398,837 filed Mar. 6, 1995, now abandoned; (2) a continuation-in-part of U.S. Ser. No. 08/550,044 filed Oct. 30, 1995, which issued as U.S. Pat, No. 5,723,690 on Mar. 3, 1998, which, in turn, is a continuation of U.S. Ser. No. 08/426,997 filed Apr. 24, 1995, which issued as U.S. Pat. No. 5,527,971 on Jun. 18, 1996; and (3) a continuation-in-part of U.S. Ser. No. 08/426,996 filed Apr. 24, 1995, now abandoned.

BACKGROUND OF THE INVENTION

This invention relates to improved, highly efficient processes for the preparation of tetrabromobisphenol-A.

Tetrabromobisphenol-A is one of the most widely used brominated flame retardants in the world. It is used extensively to provide flame retardency for styrenic thermoplastics and for some thermoset resins.

U.S. Pat. No. 5,527,971 (its Background of The Invention is incorporated herein as if fully set forth) discloses highly beneficial techniques for the continuous and batch production of tetrabromobisphenol-A without concomitant production of alkyl bromide. In addition, these techniques produce a tetrabromobisphenol-A product having good color and low hydrolyzables and ionics. The process yield is excellent.

As is always the case in commercial endeavors, it is desirable to provide for improvements which benefit process aspects and/or which give a superior product. Therefore, it is an object of this invention to provide for these ends.

THE INVENTION

This invention relates to a process for producing tetrabromobisphenol-A, which process comprises:

(a) feeding, to a reactor, a solution comprised of bisphenol-A, water and a water miscible solvent to at least partially form a reaction mass having a liquid phase containing from above about 15 to about 65 wt % water, the wt % being based upon the amount of water and water miscible solvent in the liquid phase;

(b) during (a), feeding a stream of gaseous bromine to the reaction mass, such gaseous feed stream having a Reynold's number ≧40,000;

(c) during (a), providing for the presence, in the reaction mass of (i) from about 50 to 20,000 ppm unreacted bromine and (ii) less than about 20 wt % HBr, the ppm and wt % HBr values being based upon the total weight of the liquid phase of the reaction mass; and (d) during (a), forming a reaction mass precipitate phase which comprises at least about 95 wt % tetrabromobisphenol-A, the wt % being based on the total weight of the precipitate phase.

It has been found that when the liquid phase of the reaction mass contains less than about 20 wt % HBr, consistently obtaining a good tetrabromobisphenol-A color is enhanced by adding the bromine reactant to the reaction mass as a gaseous stream having a Reynold's number ≧about 40,000. The use of a liquid or a part liquid and part gaseous bromine stream will give poor color. Also, the use of a Reynold's number less than about 40,000 will not give the best color on a consistent basis. The lower the wt % HBr in the liquid phase of the reaction mass, the more pronounced is the benefit obtained by using a gaseous bromine feed stream with a Reynold's number ≧40,000. When the HBr wt % is from about 5 to about 17, the APHA color of the tetrabromobisphenol-A product, is benefited from about 50% to about 300%, the greatest points of improvement occurring at the lower end of the HBr wt % range. In addition, the tetrabromobisphenol-A product is further benefited by a gaseous bromine feed with high Reynold's number as the ionics content of the tetrabromobisphenol-A product is also lower, say less than about 100 ppm, based on the total weight of the product. A Reynold's number ≧40,000 also makes the reaction system more robust in the sense that the reaction is not overly sensitive to an excess bromine content in the liquid phase of the reaction mass, such excess normally being expected to adversely affect product color.

For the purposes of this invention, the term, "gaseous bromine stream," means that the stream is of bromine gas in which there is no visible liquid bromine. The bromine gas stream can be monitored for visible liquid bromine via a sight glass in the bromine feed line upstream of its feed point. If liquid drops, condensate or more are observed, then it can be predicted that the product produced during such a feed will have poor color, all other parameters being held constant.

The Reynold's number is a dimensionless number determined by the following formula:

$$\text{Re No.} = DV\rho/\mu$$

in which D is the diameter of the outlet orifice in feet, V is linear velocity in feet/sec., $\rho$ is the fluid density in lb/ft$^3$, and $\mu$ is the fluid viscosity in lb/(ft)(sec). For gaseous bromine $\rho=0.124$ lb/ft$^3$ and $\mu=1\times10^{-5}$ lb/(ft)(sec) at 60° C. It is preferred that the gaseous bromine stream be fed from a cylindrical orifice at the end of a dip tube which extends to a point below the surface of the liquid level of the reaction mass. The Reynold's number used in the process of this invention is measured at the discharge end(s) of the feed tube.

It is preferred that the Reynold's number be within the range of from about 40,000 to about 2,000,000, and most preferably within the range of from about 500,000 to about 1,000,000. Most highly preferred is the range of from about 600,000 to about 1,000,000.

DRAWING

FIG. 1 is a graph of the APHA color of tetrabromobisphenol-A products vs. the wt % of HBr in the liquid phase of the reaction mass used to produce the different products. Two plots are given—one for a Reynold's number of 17,000 and the other for a Reynold's number of 50,000.

DETAILED DESCRIPTION

The brominations which occur in the processes of this invention occur with great rapidity. In fact, it is believed that the rapidity with which substantially all of the bisphenol-A is tetrabrominated is another key to obtaining the highly pure products of this invention. The reaction masses used by the processes of this invention contain significant amounts of water, thus making it incumbent that the tetrabromination occur very quickly. If it should not, the prior art teaches that the presence of large amounts of water will result in the premature precipitation of tribromobisphenol-A which will denigrate the purity sought for a tetrabromobisphenol-A product. The use of the high temperatures for the processes of this invention promotes the rapid tetrabromination. However, such temperatures would normally be thought to also promote the facile production of alkyl bromide. Despite such concerns, the processes of this invention do not exhibit rampant alkyl bromide production. Instead, the processes of this invention exhibit minimum alkyl bromide production, say from about 4.54 to 0.0454 kg (10 to 0.1 lbs) or less of alkyl bromide/45.4 kg (100 lbs) of tetrabromobisphenol-A precipitate produced, such production depending upon the process parameters. Without the use of an oxidant to convert HBr to $Br_2$, and with methanol as the solvent, the methyl bromide production is typically found to be less than 1.8 kg (4 lbs) and preferably within the range of from about 1.8 kg (4 lbs) to about 0.454 kg (1 lb) or less/45.4 kg (100 lbs) of tetrabromobisphenol-A precipitate produced. With ethanol as the solvent, the alkyl bromide production can be less than 0.91 kg (2 lbs) and preferably within the range of from about 0.91 kg (2 lbs) to about 0.0454 kg (0.1 lb) or less/45.4 kg (100 lbs) of tetrabromobisphenol-A.

The bisphenol-A is preferably added to the reaction mass in a molten form or as a solute in a solution which comprises an alcohol solvent. Less preferred is the addition of the bisphenol-A as a solid. It is an important feature that the bisphenol-A be added to the reaction mass with its above-stated concentration of unreacted $Br_2$. Adding the bisphenol-A in this manner is novel and is believed to contribute to the highly desired rapid tetrabromination. With the presence of the specified unreacted $Br_2$ in the reaction mass, the bisphenol-A, as it is being fed, always has available the $Br_2$ needed for its quick tetrabromination but not so much that degradation of the bisphenol-A structure is realized. Compare the prior art which adds the $Br_2$ to a reaction mass of bisphenol-A. In this latter case, there is insufficient $Br_2$ available for tetrabromination until near the end of the $Br_2$ feed, which feed can take 0.5+ hours to effect. Even then, the prior art teaches the need for a post-curing or aging step to complete the tetrabromination. Such post-curing or aging steps entail raising the temperature of the reaction mass significantly and holding the temperature for the prescribed curing or aging period. Due to the long tetrabromination times for these prior art processes, it is not possible to use much more than about 20 wt % water in the reaction mass, as larger amounts of water will result in significant precipitation of under-brominated species, e.g., tribromobisphenol-A. Such precipitation would occur even before the $Br_2$ feed is complete.

The maintenance of the specified concentration of unreacted $Br_2$ in the reaction mass can be effected by adding the gaseous $Br_2$ to the reaction mass alone or by adding the gaseous $Br_2$ and producing $Br_2$ in situ. However the $Br_2$ is brought to the reaction mass, its concentration can be easily adjusted to the desired levels by monitoring the reaction mass for the desired $Br_2$ concentration and then adjusting the addition of $Br_2$ and/or bisphenol-A to the reaction mass. If there is to be in situ production of $Br_2$, then that production can be adjusted to compliment the adjustments to the $Br_2$ and/or bisphenol-A additions. These monitoring and adjusting methods are more fully hereinafter described. It is preferred that the gaseous bromine feed stream entry point be sub-surface of the reaction mass. This is conveniently accomplished by use of a dip tube in the reaction vessel. The use of the in situ $Br_2$ production along with direct $Br_2$ addition is also preferred. The dip tube can be fitted with a nozzle or can simply be a tube having an open end.

It is preferred that the $Br_2$ be co-fed with the bisphenol-A to the reaction mass. It is more preferred that the co-fed bisphenol-A be as a solute in a solvent comprising alcohol solvent. In a most preferred form, the solvent will also contain water. By co-feeding, it is meant that the $Br_2$ feed period and the bisphenol-A or bisphenol-A solution feed period overlap one another to at least some extent. (A feed period is that period of time over which all of a subject feed is fed to the reactor.) For example, the $Br_2$ feed can be to an initial alcohol/water charge followed by the bisphenol-A or bisphenol-A solution feed, with the $Br_2$ and later feeds thereafter occurring simultaneously until finished. Another example would be that of the same initial $Br_2$ feed followed by a continuous bisphenol-A or bisphenol-A solution feed which is accompanied by a continued, but intermittently interrupted or staged, $Br_2$ feed. Yet, another example is that of initiating the $Br_2$ feed to an alcohol and water pre-charged reactor followed by the bisphenol-A or bisphenol-A solution feed so that the two feeds occur simultaneously until the specified amount of $Br_2$ has been fed. At that point, the bisphenol-A or bisphenol-A solution feed continues alone until it is finished. Also, the $Br_2$ and bisphenol-A or bisphenol-A solution feeds can be, timewise, completely concurrent—one with the other. Other co-feeding schemes are possible, it being required that the scheme must more closely approximate the addition of the bisphenol-A to a reaction mass having the before-specified unreacted $Br_2$ concentrations than it approximates the addition of $Br_2$ to a bisphenol-A reaction mass. It is preferred that the feed periods overlap one another at least 75% of the time, and most preferred at least 90% of the time.

Commercially available $Br_2$ is suitable for use as the $Br_2$ feed. Should the $Br_2$ contain undesirable impurities, it can be treated by conventional purification techniques, e.g., distillation, $H_2SO_4$ treatment, etc., which are well known to those skilled in the art.

Processes of this invention feature the use of water in the reaction mass which is within the range of from about 30 to about 85 wt %, based upon the total amount of water and alcohol solvent in the reaction mass. Preferably, the amount of water in the reaction mass is within the range of from about 30 to about 75 wt % water. Most highly preferred is the range of from about 30 to about 70 wt %. When the alcohol solvent is methanol, the preferred amount of water is from about 30 wt % to about 55 wt %. Should the alcohol solvent be ethanol, then the preferred amount of water is from about 40 wt % to about 65 wt %.

The water content of the reaction mass is an important aspect of this invention. As before stated, it is believed, for the processes of this invention, that the water content greatly attenuates the formation of alkyl bromide while, unexpectedly, allowing for a high yield of a high purity tetrabromobisphenol-A product. It is theorized, though the processes of this invention are not to be limited by any theory, that the formation of methyl bromide or ethyl bromide is attenuated because the HBr, which is co-produced by the substitution bromination reaction between the aromatic moieties of bisphenol-A and $Br_2$, is diluted by the large amount of water in the reaction mass. Further, the HBr reacts with the water to yield $H_3OBr$ which is very slow to react with the alcohol in the reaction mass. As pointed out previously, the attenuated alkyl bromide formation for the processes of this invention does not generally exceed about 4.54 kg (10 lbs) of alkyl bromide/45.4 kg (100 lbs) of tetrabromobisphenol-A precipitate produced.

With regard to the high yield of a highly pure tetrabromobisphenol-A product, it is noted that typical products from the processes of this invention have a tetrabrombisphenol-A purity of at least 95 wt %, based on the total weight of the recovered product, and a tetrabromobisphenol-A yield of at least 90%, based on the bisphenol-A fed. This yield and purity are believed to be due to the large concentration of water in the reaction mass. Without being limited to any particular theory, it is believed that the water enhances the presence of brominating species in the reaction mass. With this enhancement, there is a favoring of the rapid bromination of the bisphenol-A all of the way to tetrabromobisphenol-A, all before the intermediate, tribromobisphenol-A, has sufficient opportunity to form a significant amount of precipitate. It is believed that the enhancement of the brominating species is due to the fact that, as before stated, HBr reacts with water to form the $H_3OBr$ acid. The $H_3OBr$ acid does not react as readily with $Br_2$ as does HBr. This is important because, if $H_3OBr$ was not formed, a larger quantity of HBr would be available to react with $Br_2$ to form $HBr_3$. The $HBr_3$ is not desired as it is a weak brominating species in the reaction mass and its formation consumes $Br_2$. With less $Br_2$ available, there is a slowing of the bromination reaction. This slowing can result in an increase in the precipitation of tribromobisphenol-A.

The water in the reaction mass can be supplied thereto by simply being fed to the reactor as a direct water feed or it may be supplied as a constituent of the bisphenol-A/alcohol solvent solution or it may be supplied via a direct water feed and as a constituent of the bisphenol-A/alcohol solvent solution. Supplying the water as part of such a solution is convenient and preferred. If the water is introduced to the reaction mass as a separate feed stream, then it may or may not be fed essentially contemporaneous with the feed of the bisphenol-A/alcohol solvent solution. Even further, a portion, if not all, of the water can be fed as steam or steam condensate along with a gaseous $Br_2$ feed. The steam could have been used to vaporize the $Br_2$ to form the gaseous feed. Another example features supplying water as a charge or as part of a charge to the reactor prior to initiating the feeds and adjusting the amount of water later fed to obtain the desired water content in the reaction mass. When hydrogen peroxide is used in the process, a portion of the water can be supplied along with hydrogen peroxide feed. Also, the use of hydrogen peroxide will result in the formation of water as it oxidizes the HBr. This water of oxidation can also be used as a water source. However the water is supplied to the reaction mass, it is preferred it be such that the proper amount of water be present in the reaction mass during substantially all of the bisphenol-A feed.

In those cases where the amount of water used is in the lower end of the range, say 30 to 35 wt %, and the other process parameters have not been optimally selected, it may be desirable to add some additional water at the end of the bisphenol-A feed. The possible advantage to such an addition is that the additional water may cause further precipitation of tetrabromobisphenol-A from the reaction mass. The further precipitation goes towards increasing the yield of the process.

The alcohol solvent can be supplied as an individual feed or as a solvent constituent of the bisphenol-A solution feed or as both. From a practical standpoint though, the alcohol solvent is best fed as a solution constituent. The amount of alcohol solvent in the reaction mass is that amount which will insure, in the presence of the water, that the bisphenol-A and its under-brominated intermediates, i.e., mono-, di- and tri-bromobisphenol-A, are essentially soluble and that the desired tetrabromobisphenol-A is highly insoluble. Such amounts are referred to herein as "solvent quantities." Generally, the amount of alcohol solvent used, expressed as a weight ratio of alcohol to bisphenol-A fed, is within the range of from about 0.5:1 to about 10:1. Preferred for methanol is the range of from about 2 to about 5. For ethanol, the preferred range is from about 1 to about 4. A most preferred range for methanol is from about 2.5 to about 4. A most preferred range for ethanol is from about 1 to about 2. If the bisphenol-A is to be supplied as a solution in the alcohol solvent, then the alcohol solvent can be supplied to the reaction mass via the solution feed or as a part of the solution feed and the remainder via a separate alcohol feed. The amount of alcohol solvent in the solution is, at a minimum, that amount which will at least provide a flowable slurry and, preferably, a free-flowing liquid. The practitioner can empirically determine the minimum amount needed for the particular alcohol and feed temperature chosen.

When choosing the weight ratio of alcohol to bisphenol-A fed, it should be noted that the lower ratios, say 1.3 to 2, can result in a high concentration of HBr in the reaction mass. Reaction mass concentrations of HBr much in excess of 35 wt % are generally to be avoided. It is believed that HBr concentrations of 35+ wt %, especially 40+ wt %, can cause degradation of and/or inferior product. So that the practitioner can use the lower alcohol to bisphenol-A weight ratios, it is desirable to attenuate the HBr concentration in the reaction mass by feeding an oxidant to the reaction mass, e.g., $H_2O_2$ or $Cl_2$, to oxidize the HBr to $Br_2$. In this way, the HBr concentration is attenuated and $Br_2$ is made available to the reaction mass, this latter effect reducing the amount of $Br_2$ that needs to be fed to the reactor.

In a most preferred form, the bisphenol-A is fed as a solute in solution with an alcohol solvent and water. The most highly preferred mode of operation is to supply essentially all of the bisphenol-A, alcohol solvent and water to the reaction mass via such a solution. (Some water can be introduced to the reaction mass as the result of the formation of alkyl bromide and in those cases where $H_2O_2$ is used to oxidize HBr to $Br_2$. This water goes towards the total water in the reaction mass.) Such a preferred mode simplifies insuring the proper reaction mass composition. Indeed, it is most preferred that the bisphenol-A/alcohol solvent/water solution substantially mimic the alcohol solvent/water composition of the reaction mass, say within 75% of the composition reaction mass. Thus, a preferred solution will contain from about 30 to about 85 wt % water, based upon the weight of the alcohol solvent and water. Other preferred ranges mimic the preferred ranges for the reaction mass.

The alcohol solvent is a $C_1$ to a $C_4$ alcohol which, in the prescribed amount, is capable of dissolving the $Br_2$, bisphenol-A, monobromobisphenol-A, dibromobisphenol-A and tribromobisphenol-A under reaction conditions. The reaction conditions of special import are the reaction mass temperature, the presence of unreacted $Br_2$ in the reaction mass and the reaction mass water content. Further, the alcohol should be substantially inert with regard to $H_3OBr$ and the ar-bromination of the bisphenol-A to tetrabromobisphenol-A. The alcohol also should not contribute to the production of troublesome amounts of color bodies, ionic bromides and/or hydrolyzable bromides. Hydrolyzable bromides include 1-bromo-2-methoxy-2-(3', 5'-dibromo-4'-hydroxyphenyl)propane, 1,1-dibromo-2-methoxy-2-(3',5'-dibromo-4'-hydroxyphenyl)propane, 1,3-dibromo-2-methoxy-2-(3',5'-dibromo- 4'-hydroxyphenyl) propane, and 1,1,3-tribromo-2-methoxy-2-(3',5'-dibromo-4'-hydroxyphenyl)propane. The alcohol, when taken in combination with the water and reaction conditions of the processes of this invention, can have some small ability to dissolve tetrabromobisphenol-A, but for the sake of reaction yield, the dissolving power should be low, say no more than about 10 wt % and preferably no more than about 5 wt % dissolved tetrabromobisphenol-A in the liquid phase of the reaction mass, the weight percent being based on the weight of the liquid phase.

Exemplary of the preferred alcohol solvents are methanol, ethanol, propanol, butanol and mixtures of any two or more of the foregoing. Polyhydric alcohols such as ethylene glycol and glycerine and any mix of the foregoing are also suitable. Further, any mix of any of the alcohols of this invention is suggested. Most preferred are methanol, ethanol and propanol, with methanol and ethanol being the solvents of choice. Methanol and ethanol are relatively inexpensive and are easily recovered by simple distillation techniques for recycle. Since there is a large water presence in the processes of this invention, it is not necessary to recover the alcohol with a low water content, thus reducing the alcohol recovery cost. If ethanol is used, the denaturate should be selected to not yield additional by-products to the system. A preferred denaturate is ethyl acetate as it does not introduce a new by-product to the system.

When choosing the alcohol to be used, the practitioner should consider that the alcohol chosen will determine the alkyl bromide produced. Hence, methanol will yield methyl bromide, and ethanol will yield ethyl bromide. Even though the amount of alkyl bromide produced by the processes of this invention is small, there still may be some preference for the alkyl bromide produced and that preference might be addressed by the alcohol chosen. The most preferred alcohol is ethanol.

The reaction mass is essentially a two-phase system—a liquid phase and a solid phase. The former will comprise the reactants, by-product HBr, the alcohol solvent and the water, while the latter will comprise the tetrabromobisphenol-A precipitate. The reaction mass is absent of any need for a second liquid phase, such as that which could be provided by a water immiscible organic compound, see U.S. Pat. No. 3,929,907. The volume of the liquid phase is generally defined by the amount of alcohol solvent and water present, the other constituents only making a minor contribution. The liquid phase volume should be consistent with providing a stirrable and manageable reaction mass but not so large that the volume burdens the process with a need for an overly large reactor and a materials handling problem.

The feed streams are preferably at a temperature which promotes efficient obtainment of the desired reaction mass temperature. A suitable gaseous $Br_2$ feed stream temperature is from about its boiling point to about 120° C. A preferred range is from about 80° C. to about 110° C. The bisphenol-A/alcohol solvent solution and/or the individual feed temperatures should be that which do not detrimentally cool or heat the reaction mass and which allow for the feeds, except for the gaseous bromine, to be made in the liquid state.

The $Br_2$ and bisphenol-A/alcohol solvent solution and/or separate feeds all contribute to the formation of the reaction mass in the reactor. A portion of the $Br_2$ fed to the reactor and/or produced in situ will be consumed in the bromination reaction. The non-consumed $Br_2$ preferably provides, until it in turn is consumed, for the before-described excess of unreacted $Br_2$ in the liquid phase.

As a statement of general principle, the presence of the unreacted $Br_2$ in the reaction mass is for the purpose of keeping the $Br_2$ content in the reaction mass ahead of the bisphenol-A feed, thus assuring a perbromination condition without unwanted side effects. The presence of unreacted $Br_2$ in the liquid phase is extant as bisphenol-A is being fed. It is preferred that the unreacted $Br_2$ presence be coextensive with the bisphenol-A feed. It is permissible, however, for the unreacted $Br_2$ content to stray out of the before-specified ranges for brief periods of time depending on the level of under-brominated species that can be tolerated in the tetrabromobisphenol-A reaction product and/or upon the extent of precipitation of the under-brominated species which is realized. In fact, if the period of time is very brief and favorable reaction parameters are chosen, the formation of these under-brominated precipitates may not occur to any appreciable extent at all. The practitioner will have to observe the process and determine by empirical methods the sensitivity of the chosen reaction conditions to the brief straying of unreacted $Br_2$ content from the specified ranges. Thus, for the purposes of this invention the "presence of unreacted $Br_2$," can encompass brief periods of time in which the unreacted $Br_2$ content is not within specification, but which does not result in the formation of under-brominated species to an extent that results in an unacceptable tetrabromobisphenol-A product, say one containing less that about 95 wt % tetrabromobisphenol-A.

Quantifying the preferred amount of unreacted $Br_2$ in the reaction mass liquid phase is best handled by a trial and error technique. A trial process is first defined by choosing an unreacted $Br_2$ level and the other process parameters. The produced tetrabromobisphenol-A product from the process is analyzed for its tri- and tetrabromobisphenol-A content. If the tribromobisphenol-A level is too high, another trial process is constructed with a higher unreacted $Br_2$ level or with different process parameters, say raising the reaction mass temperature or increasing the residence time. The procedure is repeated until the desired product is obtained. Caution should be taken when adjusting the process parameters to insure that the production of unwanted by-products, e.g., tribromophenol, does not become a problem. Once the desired product has been obtained, the unreacted $Br_2$ content used is then measured.

Measuring the unreacted $Br_2$ content can be performed by the use of colorimetric techniques. One technique comprises first forming an acidic (HBr) water and methanol solution. From this solution, several equivolume samples are drawn. To each sample is added a different and measured amount of $Br_2$. The colors of these sample solutions are then compared colorimetrically with the color of the reaction mass liquid phase used in the test process. A color match indicates that the $Br_2$ content in the liquid phase of the reaction mass is equal to that in the sample. Colorimetric determination for unreacted Br2 is suitable as color correlates nicely with unreacted $Br_2$ content. Low concentrations give a pale yellow color, intermediate concentrations give a strong yellow color, high concentrations give an orange color, and the highest concentrations give a dark red color. For the wide range of process conditions disclosed herein, unreacted $Br_2$ concentrations in excess of 50 ppm, but less than about 20,000 ppm, are to be considered. Preferably, the unreacted $Br_2$ content will be within the range of from about 50 to about 15,000 ppm, and most preferably within the range of from about 1,000 to about 8,000 ppm. The best range is from about 2,000 to about 6,000 ppm. The ppm values are based upon the weight of the reaction mass liquid phase (liquid portion).

Once the process parameters have been chosen, the maintenance of the unreacted $Br_2$ concentration in the reaction mass can be accomplished by measuring, during the bisphenol-A feed, the $Br_2$ concentration, e.g., by the above-described calorimetric technique, then adjusting the $Br_2$ feed, the bisphenol-A feed or both to obtain the desired $Br_2$ concentration as again determined by the colorimetric technique. Since there will be tetrabromobisphenol-A precipitate in the reaction mass, calorimetric monitoring may require that a small stream be taken from the reactor and filtered to remove the solids before being submitted to a colorimetric technique. If removal and filtration is difficult, the reaction mass color may be read by the use of reflectance techniques which measure the intensity of the light reflected off of the reaction mass. Also, color comparisons can be made by use of a portable Hunter Mini-Scan/EX colorimeter and by comparing the Hunter "a" values of the samples and the reaction mass. The "a" values appear to correlate well with the excess $Br_2$ content. The Mini-Scan/EX colorimeter operates by producing a flash of white light onto a sample. The reflected light is dispersed by a holographic grating onto a diode-array detector. Percent reflectance data is obtained every 10 nm from 400 to 680 nm. This data is used to calculate the L, a, b, and YI values. In all of the calorimetric cases, the color of the liquid phase of the reaction mass is the determinative factor.

It is to be understood that techniques other than colorimetric techniques may be used in monitoring to obtain the desired unreacted $Br_2$ level in the reaction mass. Though the particular technique used is not critical to the processes of this invention, the use of the colorimetric technique is highly preferred.

It is also to be understood that the method used to obtain the desired unreacted $Br_2$ level can be by a method other than the adjustment of the before-mentioned feeds. For example, when an oxidant is used to convert HBr to $Br_2$, the amount of $Br_2$ generated can be regulated by controlling the amount of oxidant fed to the reaction mass. The amount of unreacted $Br_2$ contributed to the reaction mass by oxidation of HBr can be substantial considering that four moles of HBr are generated for each mole of tetrabromobisphenol-A produced. Thus, when additional $Br_2$ is needed, the practitioner can use the oxidation of HBr to generate at least a part of the $Br_2$ needed to obtain the desired unreacted $Br_2$ level.

With the use of an oxidant to oxidize the HBr to $Br_2$, the processes of this invention can obtain good results by feeding only about two moles or slightly more of $Br_2$ to the reactor for every one mole of bisphenol-A fed. (When speaking of the amount of $Br_2$ fed per mole of bisphenol-A, the context is the relationship between the overall total amounts of these two feeds and is not meant to describe the relationship at any one time in the reaction mass.) The other two moles of $Br_2$ that are needed can be provided by the full oxidation of the co-generated HBr. If there is less than full HBr oxidation, then the total amount of $Br_2$ fed to the reactor will be that amount, in sum with the $Br_2$ formed by oxidation, which will provide at least stoichiometric quantities of $Br_2$ and, preferably, quantities which are in slight excess of stoichiometric, say from about 0.1% to about 3% percent of stoichiometric. Stoichiometric $Br_2$ for the ar-tetrabromination of bisphenol-A is four moles of $Br_2$ per mole of bisphenol-A. As can be appreciated, if the oxidation of HBr is not part of the process, then the $Br_2$ feed would be at least stoichiometric (four moles of $Br_2$ per mole of bisphenol-A fed), with the slight excess being preferred, e.g., up to about 4.1–4.25 moles of $Br_2$ per mole of bisphenol-A fed.

For batch processes, the excess $Br_2$ present after completion of the process can be removed by treating the reaction mass with a reducing agent, such as sodium sulfite or hydrazine, or by slowly feeding excess bisphenol-A until essentially all bromine has reacted.

If an oxidant is used to convert HBr to $Br_2$, the oxidant can be any which is capable of oxidizing HBr to $Br_2$ in the reaction mass and under the process conditions of this invention, all without deleterious affect on the production of tetrabromobisphenol-A in high purity and in high yields. Preferred oxidants are those in liquid or gas form which facilitates their feed to the reactor. Preferred oxidants are chlorine and hydrogen peroxide.

When $Cl_2$ is the oxidant, it can be fed to the reaction mass as a gas or as a liquid. The gaseous feed is preferred. To mitigate against the formation of chlorinated bisphenol-A, it is preferred that the $Cl_2$ be fed after initiation of the $Br_2$ feed. After the initial $Br_2$ feed, $Cl_2$ can be fed contemporaneously with the $Br_2$ feed. Even with this feed sequence, some bromochlorobisphenol-A compounds will be formed. Fortunately, these bromochloro species are present in very minor amounts, say from about 50 to about 500 ppm, based on the total weight of the precipitate. The most predominate bromochloro specie will, in most cases, be chlorotribromobisphenol-A.

When the oxidant is $H_2O_2$, safety makes it preferable that it be fed to the reaction mass in an aqueous solution containing no more than about 90 wt % $H_2O_2$. Preferred are aqueous solutions containing from about 30 to about 80 wt % $H_2O_2$. A most preferred solution is one containing from about 50 to about 70 wt % $H_2O_2$.

The $H_2O_2$ can be fed to the reaction mass at any time. For batch operation, it is preferred that the $H_2O_2$ be fed after most of the $Br_2$, say above about 50%, has been fed. For continuous operation, the $H_2O_2$ feed would most preferably occur contemporaneously with at least most of the $Br_2$ feed. Most preferably, the $H_2O_2$ feed would start after initiating the $Br_2$ feed.

The oxidants can be fed to the reaction mass separately or in some cases, along with the $Br_2$ feed. It is preferred that the $Cl_2$ be fed through the same feed conduit as is the $Br_2$ and may be fed while $Br_2$ is being fed. In distinction, the $H_2O_2$ is preferably fed as a separate feed stream.

The amount of oxidant fed is preferably that amount needed to oxidize that amount of HBr which is needed to yield the desired amount of $Br_2$ Both $H_2O_2$ and $Cl_2$ are capable of oxidizing HBr on a one mole to two mole basis. Thus, relating the oxidant to the bisphenol-A feed and depending upon the amount of HBr that is set for oxidation, a typical mole ratio of $H_2O_2$ or $Cl_2$ to bisphenol-A will be within the range of from about 1:1 to about 2:1. A more preferred mole ratio is from about 1.5:1 to about 1.9:1. The higher oxidant ratios are preferred when $H_2O_2$ is the oxidant, while the mid-range ratios, say 1.5–1.8:1, are preferred when $Cl_2$ is the oxidant. The reason that the lower oxidant ratios are preferred for $Cl_2$ is that there is a balance between the amount of HBr oxidized and the amount of chlorobromo species which can be tolerated. If there is no need to keep the chlorobromo species to some minimum amount, then more $Cl_2$ is permissible. Adjustments to the above ranges are necessary if the oxidant chosen does not oxidize the HBr on a one to two basis. In these cases, the ranges are adjusted in proportion to the variance in the one to two relationship.

Another important consideration in practicing the processes of this invention is the reaction mass temperature. It is desirable to use a relatively high temperature so that the bromination of the bisphenol-A to tetrabromobisphenol-A will be sufficiently fast to attenuate the formation of tribromobisphenol-A precipitate. However, there is a practical limit as to how high the temperature can be. For example, the practitioner would not want to use temperatures which would cause the production of unacceptable levels of unwanted by-products or the degradation of the tetrabromobisphenol-A product.

It is unusual to operate a tetrabromobisphenol-A process at relatively high temperatures during the addition of a reactant, that is, for the instant case, bisphenol-A. This is especially so when the production of alkyl bromide is to be minimized. It is conventional to expect that high temperatures will yield large amounts of alkyl bromide. Also, the use of high temperatures is not conventional when the precipitation of the tetrabromobisphenol-A is to occur under reaction conditions soon after it is formed—such precipitation being a feature of the processes of this invention. It would be expected that high temperatures would frustrate such precipitation by increasing the solubility of the tetrabromobisphenol-A in the solvent solution and require a final cooling of or addition of water to the reaction mass to effect the desired precipitation. The processes of this invention are not so affected, nor is there required a cooling step to obtain tetrabromobisphenol-A precipitation. In addition, the use of the higher temperatures of this invention reduce process costs as the processes can use cooling tower water to cool the reactor instead of having to use refrigeration which is required by the low temperature processes.

Preferred reaction mass temperatures are within the range of from about 30 to about 100° C. More highly preferred temperatures are within the range of from about 40 to about 100° C. The most highly preferred temperatures are within the range of from about 50 to about 75° C. Temperatures within the range of from about 50° C. to about 65° C. are best.

The bromination of bisphenol-A is an exothermic reaction as is the oxidation of HBr with an oxidant. To control the reaction mass temperature, it may become necessary to remove heat from the reaction mass. Heat removal can be effected by running the reaction at reflux with a condenser facilitating the heat removal. If it is desired to operate at a temperature below the atmospheric boiling point of the reaction mixture, the reaction can be run under sub-atmospheric pressure.

Generally, the basic concepts of the processes of this invention are not appreciably affected by the process pressure. Thus, the process can be run under sub-atmospheric, atmospheric or super-atmospheric pressure.

At process initiation, it is desirable to charge the reactor with a liquid pre-reaction charge which will become a part of the reaction mass upon the commencement of the feed. The liquid charge will provide a stirrable reaction mass and act as a heat sink to moderate temperature changes in the reaction mass. The liquid charge is preferably comprised of water and the alcohol solvent fed in the bisphenol-A solution and in substantially the same proportion. Further, it is preferred that the solvent be saturated with dissolved tetrabromobisphenol-A. It is also preferred that the reactor be charged with seed particles of tetrabromobisphenol-A. The saturation of the solvent and the presence of the seed particles both act to enhance the precipitation of the tetrabromobisphenol-A produced during the bromination period. The initial charge can be acidic, e.g., containing from 1 to 20 wt % acid, such as a hydrohalogenic acid, e.g., HBr, HCl, or the like. HBr is preferred. The acid seems to promote good color in the initial tetrabromobisphenol-A produced. It is most practical to use a heel from a previously run process of this invention as the liquid charge. The tetrabromobisphenol-A seed particles can be brought over from the previous run or can be added separately. If a heel is not available, it is also possible to use a separate pre-reaction charge of water, alcohol solvent and, if desired, the optional acid. The only caveat to this scheme is that there must be apportionment of the various feeds so that there will still be compliance with the various parameters which define the processes of this invention.

It is beneficial to insure that the reaction mass liquid portion is acidic in nature. This can be easily accomplished by allowing for a presence of HBr in the reaction mass during at least a portion of the reaction period, and preferably during all of the reaction period. If none or not all of the HBr produced from the aromatic bromination is oxidized to $Br_2$, then that HBr can act to accomplish the acidification. Generally speaking, the reaction mass liquid portion should contain from about 1 wt % to less than about 20 wt % HBr, based on the total weight of liquid portion of the reaction mass. Most preferred is the range of 7 wt % to less than about 20 wt % HBr. Most highly preferred is from about 10 to about 18 wt % HBr, with from about 11 to about 15 wt % HBr being most preferred. It is most preferred to have an acidified reaction mass at process initiation. This can be accomplished by using the before-mentioned "heel" or acid/alcohol solvent/water pre-charge. Having an initial acidic condition is more important when the process is run in the batch mode as the product produced without such a condition becomes part of the total product produced. In the continuous mode, the product produced without the initial acid condition will be produced during the first hours of process start-up. This sub-standard product can then be recovered and discarded. As the continuous process runs further, the acid build-up (due to the bromination of the bisphenol-A) in the reaction mass reaches steady state and becomes sufficient. Product produced under these acid conditions can then be recovered without contamination from the initially produced product. In the case of using an oxidant to convert the HBr to $Br_2$, care must be taken to not oxidize all of the HBr in the reaction mass and to thus leave sufficient HBr present to give the acid condition and acquire the color benefit. While HBr is the preferred acid, other mineral acids may be used, HCl, HF, HI or mixtures thereof. However, these non-bromine acids will have to be added to the reaction mass. Care must be exercised in selecting the amount of acid present. High amounts of acid will yield the better color but, it also produces a tetrabromobisphenol-A having a higher ionics content. A balance is best obtained between the two qualities by selecting an acid amount which gives the practitioner the desired product. Lower the acid content and the APHA color will rise; raise the acid content and the ionics level will rise. Thus, if a non-bromine acid is used, some of the HBr produced by the bromination reaction may need to be oxidized or removed from the reaction mass so that an excessive amount of acid is not present.

When the process of this invention is run as a batch process, the $Br_2$ and bisphenol-A feeds are fed to a stirred reactor until they are exhausted. There is no need for a post-feed cook or aging period of any significant length as, under the reaction conditions, the bromination of bisphenol-A to tetrabromobisphenol-A occurs quite rapidly. Also, since the water content of the reaction mass is so large and since the tetrabromobisphenol-A is so insoluble in the presence of such an amount of water, there is generally no need for or, at best, only a modicum of benefit is obtained by cooling the final reaction mass to obtain further precipitation. The benefit of cooling resides mainly in reducing the vapor pressure of solvated gaseous bromides, e.g., methyl bromide or ethyl bromide, in the reaction mass prior to the liquid-solids separation. There also could be some slowing of the formation of these bromides. Finally, depending on the separation technique used, cooling the reaction mass may make it easier to handle downstream from the reactor. Thus, if none of the above are of concern or relative value, then the reaction mass can be simply subjected to liquid-solids separation as soon as the bisphenol-A feed is finished. From a practical standpoint though, some time will lapse as the reaction mass will need to be transported to the separation equipment. If, however, cooling is desired, the cooling time will depend upon how the reaction mass is to be cooled and to what temperature it is to be cooled. In a laboratory setting, cooling times can range from about one to about thirty minutes.

After the recovery of the solids from the liquid, the solids are preferably washed with a solution of water and the particular alcohol used in the reaction. The washing removes essentially all the mother liquor from the solids. The mother liquor contains impurities such as tribromophenol, HBr, and hydrolyzable impurities. A typical wash can be a 30 wt % methanol or ethanol in water solution. The washed solids are then rewashed with deionized water to remove any remaining water miscible solvent from the first wash so as to minimize emission problems when drying the product.

When run in the continuous mode, the reactor is preferably a continuously stirred tank reactor. The reaction mass is being continuously formed and a portion thereof is being removed from the reactor during the reaction mass formation. The reactor design should be such that the average residence time in the reactor is sufficient to insure the tetrabromination of substantially all of the bisphenol-A. The feeds to the reactor and the precipitate removals can be interrupted so long as they are recurrent. The terms "continuous feed" and "continuous withdrawal" mean being characterized by continued occurrence or recurrence and are not meant to exclude interrupted feeds or withdrawals. Generally, such interruptions are of short duration and may be suitable depending upon the scale and design of the reactor. For example, since the tetrabromobisphenol-A precipitate will tend to settle near the bottom of the reactor, a withdrawal may be made and then stopped for a period of time to allow for precipitate build-up to occur prior to the next withdrawal. Such a withdrawal is to be considered continuous in the sense that the withdrawal does not await the completion of the reactor feeds and is recurrent. Such features are not generally thought of as being characteristic of batch processes.

Whether the continuous withdrawal is interrupted or not, the withdrawal results in a portion of the liquid and a portion of the solids in the reaction mass to be withdrawn together. The solids portion will be predominately tetrabromobisphenol-A. The solids portion can be filtered, the precipitate washed, etc., as is done for the above-described batch mode case.

The benefit of high temperatures on product purity is understood in view of studies which support the correlation between product purity and the relative rates of bromination and precipitation of the tribromobisphenol-A intermediate. Raising the temperature benefits both the reaction rate and the solubility of the tribromobisphenol-A in the reaction mass liquid phase and thus, promotes the obtainment of a pure product. An increase in $Br_2$ or an increase in the tribromobisphenol-A concentration in the liquid phase by reducing the liquid phase alcohol and water content can also increase the bromination rate of the tribromobisphenol-A, but, both present problems of their own. A high $Br_2$ concentration can cause the formation of undesirable by-products, while decreasing the liquid phase alcohol and water content will increase the HBr content of the reaction mass. The result is a reduction in the tetrabromobisphenol-A product purity.

It is expected that in the continuous mode of operation, the preferred reactor residence time should be within the range of from about 10 to about 150 minutes when using a continuously stirred tank reactor and the process conditions which are preferred for that operating mode. More preferred residence times are within the range of from about 30 to about 90 minutes. Most preferred is from about 30 to 70 minutes. Reactor residence time, as used herein, is the volume of the reactor contents divided by the flow rate at which slurry is removed from the reactor.

The tetrabromobisphenol-A product produced by the processes of this invention contains at least about 95 wt % tetrabromobisphenol-A and preferably at least about 97.5 wt % tetrabromobisphenol-A and, most preferably, at least about 98.5 wt %. The best products are those having above about 99 wt % tetrabromobisphenol-A. All wt % and ppm values are based on total weight of the dry precipitate. The product quality is excellent, having an APHA color less than about 50 (80 grams of tetrabromobisphenol-A in 100 ml of acetone). Preferably, the APHA color range is between 25 and 50. Hydrolyzable bromides are also kept low, generally below about 60 ppm and preferably less than 20 ppm. Ionics are preferably below 100 ppm. The process yields are impressive, with yields being at least about 90% and preferably within the range of from about 95 to about 99%.

As can be appreciated from the foregoing, the gaseous $Br_2$ feed, the Reynold's number for that feed, the bisphenol-A feed, the water content in the reaction mass, the reaction temperature and the $Br_2$ content in the reaction mass during the bisphenol-A feed all contribute to obtaining the desired tetrabromobisphenol-A product in an efficient manner. The selection of particular values for each of these process parameters to obtain the results desired will depend on each practitioner's needs and upon the equipment available. One practitioner may emphasize one benefit of using a process of this invention over other possible benefits. Thus, that practitioner may select different process parameter values than those selected by another practitioner who desires to highlight other benefit(s).

A preferred set of process parameters is: alcohol/BPA wt ratio of 0.7:1–5:1 (preferably about 1:1); alcohol is ethanol; $Br_2$ content in the reaction mass—about 2,000 to 6,000 ppm (preferably about 5,000 ppm); process temperature—40–60° C. (preferably about 50° C.); residence time (continuous mode)—about 30 to 70 minutes (preferably about 60 minutes); weight percent $H_2O$—about 35 to 60 wt % (preferably about 50 wt %), based on weight of $H_2O$ and alcohol solvent; and 10–20 wt % (preferably about 12 wt %) HBr. Most preferred ranges form the set of: alcohol/BPA wt ratio of 1–4; $Br_2$ content in the reaction mass—3,000 to 6,000; process temperature—about 45–55° C.; residence time (continuous mode) 50–70 minutes; weight percent $H_2O$—about 40–55 wt %, based upon weight of $H_2O$ and alcohol solvent; and 10–15 wt % HBr, based on the weight of the liquid phase of the reaction mass.

The reactors used for the processes of this invention are agitated reactors. It is preferred that the agitation be provided by a bladed agitator, e.g., a standard Pfaudler retreat blade. The agitation level, as measured in horsepower per 1,000 gal of reaction mass, can be from about 2.5 to about 8 hp/1,000 gal. The tip speed is from about 20 to about 25 ft/sec. By providing for good agitation, the particle size of the tetrabromobisphenol-A product is kept low while, at the same time, the occluded HBr content is also kept low. Occluded HBr is that HBr which is not removed from the product by simple drying.

The use of oxidation to generate $Br_2$ is particularly attractive in those cases where the oxidation is more economical than the cost of providing for an equivalent amount of $Br_2$ in the feed to the reactor. The economic advantage is usually extant in those cases where the costs of feeding four moles of $Br_2$ minus the value of recovered HBr is greater than the costs of feeding two moles of $Br_2$ plus the oxidation of the HBr.

While the foregoing descriptions of the oxidation of HBr generally speak of the HBr being oxidized in the reactor or reaction mass, it is within the scope of the processes of this invention to also remove co-produced HBr from the reactor and oxidize it outside of the reactor and to then send the so produced $Br_2$ back to the reactor.

It is also within the scope of the processes of this invention to provide HBr to the reactor from a source other than the reaction in the reactor. This non-indigenous HBr can be oxidized along with the co-generated HBr to yield $Br_2$. The $Br_2$ produced from the non-indigenous HBr can then count against the total $Br_2$ needs of the process and the appropriate adjustment in the $Br_2$ feed can be made. The non-indigenous HBr feed can also be adjusted to insure an acidic reaction medium despite the oxidation of HBr.

EXAMPLES

The following Examples illustrate principles of processes of this invention.

In Examples I–IX a pre-reaction charge or "mother liquor" was used which essentially contained water, methanol, HBr and much smaller amounts of impurities. Generally, the mother liquor contained about 30 wt % water and about 55 wt % methanol and about 8–20 wt % HBr.

The mother liquor used in Examples I–II came from TBBPA made as described in U.S. Pat. No. 4,628,124 by Mitchell and McKinnie.

In Examples III–VI, different mother liquors were used. The mother liquors used in Examples III and IV came from a series of previous experiments in which tetrabromobisphenol-A was produced by the reaction of bisphenol-A and bromine in a reaction mass containing methanol and water. These previous experiments were either not of this invention (water amounts, temperature, etc., were outside of defined parameters) or gave conflicting and inconclusive results. The mother liquor from the first experiment not of this invention was used in the second experiment and so on. The mother liquor from the last experiment provided the mother liquor for Example III.

In all Examples, unless otherwise indicated, the % associated with a product is to be taken as gas chromatography (GC) area percent. GC analyses were performed on a 5 Meter×0.53 mm HP-1 megabore capillary column of 2.65 micron film thickness using split injection. The column was operated from 100° C. to 300° C. with heating at 10° C. per minute. A flame ionization detector was used.

Examples I–III illustrate the production of a high-quality tetrabromobisphenol-A product with the concomitant oxidation of co-produced HBr to $Br_2$, which $Br_2$ was used to contribute to the bromination of bisphenol-A to the desired tetrabrominated product.

In Examples X and XI, each run began with a pre-charge in the reactor having a 1:1 mixture (weight basis) of ethanol and water. The reactor was run continuously for a time sufficient (which is generally 5 to 10 reactor residence times) to reach a steady state production of tetrabromobisphenol-A.

Example I

A one liter round bottom flask was equipped with a mechanical stirrer, condenser, thermometer, addition funnel, heating mantle, and fitted with a 0.3175 cm (⅛ inch) O.D. dip tube for feeding bromine and a 0.3175 cm (⅛ inch) feed tube, which terminated in the vapor space, for feeding bisphenol-A solution. The flask was charged with 200 ml of mother liquor containing 9.5 wt % HBr and about 5.0 grams of tetrabromobisphenol-A. The added tetrabromobisphenol-A acted to saturate the mother liquor and to provide seed particles to aid in the precipitation of tetrabromobisphenol-A to be produced.

A solution comprised of 100 grams of bisphenol-A, 300 ml of methanol (2% water) and 200 ml of water was prepared. 143 grams (46 ml) of $Br_2$ was placed in a vaporizer consisting of a 250 ml heated flask that had a nitrogen inlet and a gas outlet connected to the 0.3175 cm (⅛ inch) dip tube in the reactor. The pre-reaction charge of mother liquor and tetrabromobisphenol-A was brought to a temperature of about 55° C. $Br_2$ feed was started by purging nitrogen (about 200 to 500 ml/min) through the vaporizer and heating the liquid bromine. As soon as the pre-reactor charge took on a yellow color, the solution feed was begun by use of a peristaltic pump. The $Br_2$ feed was kept stoichiometrically ahead of the bisphenol-A feed by variation of the pumping rate, and as a result, the reaction mass had a yellow color. The feeds continued for 1 hour and 15 minutes when the $Br_2$ feed was finished. The solution feed was continued until the liquid phase of the reaction mass was colorless. The addition funnel was charged with 100 grams of aqueous $H_2O_2$ (30 wt %) and dropwise addition was initiated with the continued feed of the bisphenol-A solution. The aqueous feed and the solution feeds were periodically adjusted to keep the liquid portion of the reaction mass a yellow color. The reaction mass temperature was kept at 60–63° C. during the aqueous $H_2O_2$ feed. After all of the $H_2O_2$ was added, the reaction mass was yellow. Continued addition of the bisphenol-A solution would turn the mass light yellow, but the deeper yellow would return upon cessation of the solution feed. During this period, the reaction temperature was 58–62° C. Finally, 20 minutes after cessation of the aqueous hydrogen peroxide feed, the bisphenol-A solution was added until the reaction mass was colorless. The reaction mass was held at a temperature of 60–65° C. for about one-half hour and then cooled to about 55° C. The reaction mass precipitate was separated from the mother liquor by filtration and then washed with 125 ml of 20 wt % methanol in water solution. A second wash with deionized water was performed. The washed precipitate was dried and analyzed. GC analysis showed 0.64% tribromobisphenol-A and 99.3% tetrabromobisphenol-A. The mother liquor was found to contain 3.7 wt % HBr.

Example II

A one liter round bottom flask was equipped as above except there was no addition funnel and in the line from the bromine vaporizer to the connection to the dip tube was a tee for addition of chorine gas. Mother liquor (150 grams) and 3 grams of solid tetrabromobisphenol-A were added to the flask and heated to a temperature of about 55° C. A $Br_2$ vapor and $N_2$ feed was started to the flask via the dip tube followed by the feed of a solution prepared from 80.0 grams bisphenol-A, 400 ml of methanol (2 wt % water) and 200 ml of water. The total amount of $Br_2$ to be fed was 141 grams. After a few minutes, a slight gaseous $Cl_2$ feed was started. The liquid portion of the reaction mass was kept yellow by adjusting the bisphenol-A and $Cl_2$ feeds. All of the $Br_2$ had been fed in about 1.5 hours. The $Cl_2$ feed was increased to above 90 ml/min and was adjusted continuously to keep the liquid portion of the reaction mass yellow as bisphenol-A was fed at about 6 ml/min. All of the Cl₂ and bisphenol-A was fed after 2 hours. After 2 minutes from the cessation of these feeds, 2 drops of hydrazine (66 wt %) was added to destroy excess Br₂. The hydrazine rendered the liquid portion of the reaction mass colorless. The reaction mass was cooled to 20° C. The precipitate was collected and washed with 125 ml of 30 wt % methanol in water. A second washing with deionized water yielded a wet cake which was then oven dried at 120–130° C. to yield 189.8 grams of product. GC analysis showed 0.79% tribromobisphenol-A, 0.01% chlorotribromobisphenol-A, 0.04% o,p-tetrabromobisphenol-A and 99.1% tetrabromobisphenol-A.

Example III

A one liter flask was equipped as in Example IV with bromine being fed as in Example IV, except that there was placed in the nitrogen feed a tee for the addition of chlorine gas. The reactor was charged with 150 ml of a mother liquor obtained from a reaction mixture similar to Example II. This was heated to about 55° C. and addition of bromine vapor initiated. When the reaction mass took on a yellow color, the addition of a solution prepared from 90.0 grams of bisphenol-A, 450 ml of methanol, and 180 ml of water was started. After five minutes, the addition of 150–200 ml per min of chlorine gas was begun. The reaction mixture was kept at about 55° C. and was kept a yellow color by adjusting the solution flow rate. After an additional 20 minutes, chlorine flow was increased to about 250 ml per minute and after an additional 30 minutes, chlorine flow was increases to 300 ml per minute. 20 minutes later, all bromine had been added. 47 ml of bromine had been added. Chlorine flow rate was increased to maintain the reaction mass as a yellow color. Eight minutes later, all solution had been fed, at which time chlorine addition was discontinued. After seven minutes, about 2 ml of saturated sodium sulfite solution was added to destroy bromine. The reaction mixture was then cooled to 30° C. The solids were separated from the mother liquor by filtration and then washed on the filter with 125 ml of 30% methanol and then 125 ml of deionized water. The solid was oven dried leaving 209.2 grams that by GC analysis was 1.25% tribromobisphenol-A, 0.013% chlorotribromobisphenol-A, and 98.7% tetrabromobisphenol-A. The solid had an acetone color (80 grams in 100 ml of acetone) of 20 APHA, 6 ppm ionic bromide, and 16 ppm hydrolyzable bromide. Analysis of the mother liquor showed it to contain 0.09 wt % tribromophenol, 0.21 wt % tetrabromobisphenol-A, about 3 ppm tribromobisphenol-A, and about 0.04 wt % other phenolic impurities.

The following Examples illustrate principles of processes of this invention, which processes do not feature the oxidation of HBr to provide for reactant Br₂.

Example IV

A one liter round bottom flask was equipped with a mechanical stirrer, condenser, thermometer, heating mantle, and fitted with a 0.3175 cm (⅛ inch) O.D. dip tube for feeding bromine and a 0.3175 cm (⅛ inch) feed tube, which termination in the vapor space, for feeding bisphenol-A solution. The flask was charged with 150 ml of a mother liquor and 5.0 grams of tetrabromobisphenol-A. The added tetrabromobisphenol-A acted to saturate the mother liquor and to provide seed particles to aid in the precipitation of tetrabromobisphenol-A to be produced.

A solution comprised of 59.93 grams of bisphenol-A, 360 ml of methanol (2% water) and 123 ml of water was prepared. 168.2 grams of Br₂ was placed in a vaporizer consisting of a 250 ml heated flask that had a nitrogen inlet and a gas outlet connected to the 0.3175 cm (⅛ inch) dip tube in the reactor. The pre-reaction charge of mother liquor and 5 grams of tetrabromobisphenol-A was brought to a temperature of about 67° C. Br₂ feed was started by purging nitrogen (about 200 to 500 ml/min) through the vaporizer and heating the liquid bromine. As soon as the pre-reactor charge took on a yellow color, the solution feed was begun by use of a peristaltic pump. The Br₂ feed was kept stoichiometrically ahead of the bisphenol-A feed by variation of the pumping rate, and as a result, the reaction mass had an orange color. The feeds continued for 1 hour and 38 minutes when the Br₂ feed was finished. About 20 ml of the solution feed was left which was not added. After the solution feed was finished, the reaction mass was held for an additional 20 minutes at about 67–69° C. The reaction mass was colorless. The solids were collected by filtration and washed with 30% methanol in water then water and dried at a temperature of about 125° C. Gas chromatography (GC) showed the solids were comprised of 0.22% tribromobisphenol-A and 99.8% tetrabromobisphenol-A.

Example V

Essentially the same procedure was followed as in Example IV, except where noted. Mother liquor (150 ml), obtained from the filtrate of Example IV, and 5 grams of tetrabromobisphenol-A were charged to the flask at the beginning. The feed solution was made from 80.0 grams bisphenol-A, 400 ml of methanol and 210 ml water. 225.4 grams of Br₂ were used. The solution was fed at about 6 ml/min and the Br₂ was fed with a N₂ sweep at 200–500 ml/min. The reaction mass was kept at a temperature of 55–60° C. and was kept a dark yellow color by slight variation of rates of the feeds. The solution and Br₂ feeds were completed essentially at the same time. The flask from which the solution was fed was washed with 10 ml of methanol. The wash liquid was then fed to the reaction flask. The resultant reaction mass had a light yellow color after the wash liquid feed and five minutes from the stoppage of the solution and Br₂ feeds. Three drops of 63% hydrazine were added to the reaction flask to deactivate any remaining Br₂. The reaction mass was stirred for 1.5 hours without the addition of heat then the solids collected by filtration and washed with an aqueous 40% methanol solution then water. GC showed the solids to contain 0.02% tribromophenol, 0.84% tribromobisphenol-A and 99% tetrabromobisphenol-A.

Example VI

The same procedure was followed as in Example V, except where noted. The mother liquor (150 ml) came from the filtrate of Example IV. Three grams of tetrabromobisphenol-A were used with the mother liquor. The solution contained 80.16 grams of bisphenol-A, 380 ml of methanol and 300 ml of water. 225.1 grams of Br₂ were fed. The mother liquor was heated to 55° C. and then the Br₂ and solution feeds were started. The reaction mass was kept yellow by adjusting the Br₂ feed. The two feeds were finished in about two hours, the reactor temperature being maintained at 55–60° C. throughout the additions. The solution container was rinsed with about 10 ml of methanol which then was added to the reaction flask. The reaction mass was then light yellow. About 7 minutes after the feeds were finished (and the methanol rinse liquid was added), 2 drops of hydrazine were added to the reaction mass. The reaction mass became colorless. The reaction mass was left to cool to room temperature and settle. A sample of the liquid portion of the reaction mass was taken. Analysis by dilution with water and extraction with methylene chloride followed by GC analysis using tetradecane as internal standard showed that the liquid contained 0.036 wt % tribromophenol, 0.040 wt % tetrabromobisphenol-A, about 0.001 wt % tribromobisphenol-A and about 0.027 wt % other impurities, which corresponds to a yield loss of about 0.5% of theory.

The washed and dried solids recovered from the reaction mass where shown by GC to contain 1.8% of tribromobisphenol-A and 98.2% tetrabromobisphenol-A.

Example VII

A 2 liter round bottom flask was equipped as in Example IV, except the liquid bromine and a nitrogen stream (30–100 ml/min) were fed to a 1.83 meter (6 ft) length of 0.635 cm (¼ inch) Teflon tubing held in boiling water to vaporize the bromine. This vaporized bromine was then fed to the 0.3175 cm (⅛ inch) dip tube. A pre-reaction charge was formed by adding 18 ml of $Br_2$ over 20 minutes to a 2 L reactor which already contained 20 grams of bisphenol-A and 100 ml of methanol. The reactor contents were heated to reflux during the Br2 addition and so maintained for 5 minutes after the $Br_2$ feed was completed. 100 ml of water was then added to the reactor. The resultant reactor contents comprised the pre-reaction charge.

Subsequent to the formation of the pre-reaction charge, there was added, over one hour, a co-feed comprised of 94 ml of liquid $Br_2$ and about 1400 ml of a bisphenol-A solution prepared from 130 grams of bisphenol-A, 650 ml of methanol and 950 ml of water. During the co-feed the reaction mass was a yellow to orange color and was kept at a temperature of 57–60° C. Additional bisphenol-A solution (about 3 ml) was added after the co-feed until the reaction mass turned light yellow. The reaction mass was cooled to about 35° C. and filtered to yield a precipitate which was washed with a 30% aqueous methanol solution. Then the precipitate was washed with 250 ml of deionized water. After oven drying, the precipitate was weighed and was found to weigh 295 grams. GC analysis found 0.03% tribromophenol; 1.16% tribromobisphenol-A, 0.064% o,p-tetrabromobisphenol-A and 98.7% tetrabromobisphenol-A.

Example VIII

A 500 ml flask was equipped as in Example VII, including the bromine addition method of Example VII. There was included also a 0.635 cm (¼ inch) Teflon dip tube attached to a pump for removing reaction mixture. This pump, capable of pumping 167 ml per min, was attached to a timer such that it pumped reaction mixture from the flask only about 3 seconds of every 45 seconds.

The reactor was charged with 400 ml of reaction mixture from a previous run and heated to 67° C. The addition of bromine vapor was then begun. As soon as the mixture turned yellow, the addition of a solution of bisphenol-A (1000 g. bisphenol-A in 5200 ml of MeOH [3.74% water] and 1670 ml of water) was begun at a rate of about 12 ml/min. Fractions of the reaction mixture were collected in Erlenmeyer flasks that contained ½ ml of 63% hydrazine. The bromine feed rate was controlled to keep the reaction mixture yellow and the reaction temperature was maintained at 69–71° C. The reactor level was maintained at about 400 ml by small adjustments of the rate at which the reaction mixture was pumped from the flask. After fractions were collected, they were separated from the mother liquors by filtration and the solids washed with 30% MeOH and then deionized water on the filter. Table I gives the results. Sample No. 5 was collected without added hydrazine. Analysis of it's mother liquor showed 360 ppm bromine. GC analyses of two of the mother liquors on a 5 meter HP-1 megabore capillary column using tetradecane as internal standard, are shown in Table II.

TABLE I

| Sample | Time Sample Collected, minutes | Volume of Sample Ml | % $Br_3BPA$ | % TBBPA |
|---|---|---|---|---|
| 1 | 0 to 75 | 1000 | 1.0 | 98.9 |
| 2 | 75 to 152 | 1000 | 1.0 | 98.9 |
| 3 | 152 to 306 | 2000 | 1.2 | 98.8 |
| 4 | 306 to 382 | 1000 | 1.2 | 98.7 |
| 5 | 382 to 527 | 1900 | 1.2 | 98.7 |

$Br_3BPA$ - tribromobisphenol-A
TBBPA - tetrabromobisphenol-A

TABLE II

ANALYSIS OF MOTHER LIQUOR

| GC Retention Time, min. | Compound | No. 3 Sample mother liq. | No. 5 Sample mother liq. |
|---|---|---|---|
| 5.17 | TBP | 0.040 wt % | 0.042 wt % |
| 9.76 | Unknown | 0.016 wt % | 0.017 wt % |
| 9.97 | Hydrolyzable impurity | 0.025 wt % | 0.027 wt % |
| 12.61 | DBBPA | 0.031 wt % | 0.001 wt % |
| 14.99 | $Br_3BPA$ | 0.20 wt % | 0.025 wt % |
| 17.15 | TBBPA | 0.53 wt % | 0.42 wt % |
| Total, wt % | | 0.84 wt % | 0.53 wt % |
| % Yield Loss | | 2.6 | 1.6 |

TBP - tribromophenol
DBBPA - dibromobisphenol-A
$Br_3BPA$ - tribromobisphenol-A
TBBPA - tetrabromobisphenol-A

Example IX

A one liter round bottom flask was equipped as in Example IV, except temperature control was provided by a circulating bath on the jacket of the flask. The bromine was vaporized as in Example VII except heat was added by electric heating tape controlled with a laboratory variac. Additionally, a 35% $H_2O_2$ aqueous solution was added using a peristaltic pump through an 0.3175 cm (⅛ inch) O.D. tube terminating in the reactor vapor space. There was also a 0.9525 cm (⅜ inch) diameter glass dip tube added to the reactor which was attached to a sealed receiving flask by a jacketed, heated tube sloped so that gravity enhances the flow. A vacuum is periodically pulled on the receiving flask by a peristaltic pump, capable of pumping 167 ml per min, attached to a timer so that it pumped only about 7 seconds of every 147 seconds. This modification from Example VIII was necessary to consistently withdraw the approximately 60% by weight solids slurry from the reactor.

A pre-reaction charge of 400 ml existed in the reactor from previous experimental work. The mixture comprised TBBPA particles, ethanol, water, and HBr in approximately the same proportions as would be generated by the feed streams. The mixture was heated to 40° C. before the addition of bromine was begun at 1.15 ml/min. As soon as the mixture turned yellow, the addition of a solution of bisphenol-A (relative ratio of 100 g. bisphenol-A in 75 grams absolute ethanol) was begun at a rate of 3.75 ml/min.

The 35% $H_2O_2$ solution feed was then begun at 1.30 ml/min. All the necessary water was provided by the $H_2O_2$ solution, either as water or a product of the HBr reoxidation reaction. The temperature of the reaction mixture rose rapidly to 72° C. upon starting the feeds of bisphenol-A and $H2O_2$, and fell to 66° C. as the run progressed. The slight changes in the $H_2O_2$ or bromine feed rates were made to keep the reaction mixture yellow. Fractions of the reaction mixture were collected in the receiving flasks whose size matches the liquid volume in the reactor (400 ml). When full, these receiving flasks are removed from the system, and the excess bromine is quenched by adding 35% hydrazine aqueous solution dropwise.

The collected fractions were separated from the mother liquors by filtration and the solids washed with 30% EtOH and then deionized water on the filter. The resulting solids were oven dried, dissolved in acetone, and analyzed by GC to determine the TBBPA purity.

Fraction 3, represent the third residence time in the reactor, had a product purity of 99.6% TBBPA, 0.4% Br$_3$BPA, average particle size of 137 microns. The mother liquor contained 0.54% TBP and 0.35% TBBPA.

Fraction 4 had a product purity of 99.3% TBBPA, 0.7% Br$_3$BPA, average particle size of 152 micron. The mother liquor contained 0.45% TBP and 0.31% TBBPA. The reaction mass was found to be 58% solids by weight.

Fraction 5 had a product purity of 99.2% TBBPA, 0.8% Br$_3$PPA, average particle size of 156 micron. The mother liquor contained 0.43% TBP and 0.34% TBBPA.

The increase in the relative amount of TBP in the mother liquor over previous work is not due to an increase in production rate, but rather to the small amount of solvent present in this run. The solid samples did not show any significant TBP present other than trace amounts.

Example X

A 20 gallon Pfaudler, glass lined reactor was equipped with an overhead condenser, mechanical agitator, temperature and pressure indication, a diptube for feeding vapor bromine below the liquid level, mass flow control on each feed stream, and a steam heated, shell and tube bromine vaporizer. The reactor was charged with a 1:1 by weight mixture of ethanol and water to a level which submerged the end of the vapor bromine dip tube. A feed solution of bisphenol A dissolved in ethanol and the bromine feed were started when the desired reactor pressure was achieved to give the desired boiling temperature of the final reaction mass. After sufficient time is allowed for the HBr level to build to greater than 10 wt % in the liquid phase, the hydrogen peroxide feed was started at a value to achieve the desired % HBr in the final reaction mass. Water was added to achieve the desired solvent phase composition in the final reaction mass. The feed rates of each of the reactants and solvents are chosen based on a steady state mass balance which achieves the desired conditions in the reactor at the steady operating mode. Slurry is periodically withdrawn from the reactor by a pump and fed to a centrifuge where the mother liquor is separated from the solids, the solids are subsequently washed to remove impurities, and the wet solids are discharged for further processing to final product form.

The importance of the vapor bromine dip tube Reynold's number is evident in the following comparative runs. The steady state reactor conditions for each run are as follows:

| Reactor Variable | Run 1 | Run 2 |
| --- | --- | --- |
| Bromine Reynold's number | 17000 | 50000 |
| Temperature, ° C. | 60 | 60 |
| Pressure, psia | 5.9 | 5.9 |
| Residence Time, hr | 1.5 | 1.1 |
| wt % Solid in Slurry | 50 | 50 |
| Ethanol to Water Ratio | 1.1:1 | 1.1:1 |
| wt % HBr in Liquid Phase | 13 | 12 |
| Agitator rpm | 330 | 330 |
| wt % Bromine in Liquid Phase | 1.5% | 1.5% |
| Key Product Properties | | |
| % TBBPA | 99.7 | 99.1 |
| Acetone Color | 150 | 60 |

The product properties were measured after the reactor achieved steady state operation, typically greater than 5 residence times of the reactor. The product properties were constant with time once the steady operation was achieved. These two comparative runs demonstrate that the higher the Reynold's number for the gaseous bromine feed, the lower the Acetone Color achieved in the product for the reactor conditions.

Example XI

The equipment and procedure in Example X was followed several times, but the reaction variables were adjusted to fall within the following ranges:

| Reactor Variable | Range |
| --- | --- |
| Bromine Reynold's number | 17000 or 50000 |
| Temperature, ° C. | 50 to 80 |
| Pressure, psia | 4.0 to 14.7 |
| Residence Time, hr | 0.8 to 3 |
| wt % Solid in Slurry | 45 to 60 |
| Ethanol to Water Ratio | 0.8:1 to 1.1:1 |
| wt % HBr in Liquid Phase | 5 to 20% (see graph) |
| Agitator rpm | 220–330 |
| wt % Bromine in Liquid Phase | 0.2 to 1.5% |

Product purities were typically greater than 98% TBBPA. The acetone color of the various products are shown in FIG. 1. As is evident from the Figure, the bromine dip tube Reynold's number is the dominant effect on acetone color when the HBr in the liquid phase of the reaction mass is less than about 20 wt % HBr. The higher the Reynold's number, the lower the product APHA color.

As can be appreciated from the above and when viewed in their broadest aspects, the processes of this invention effect the high yield production of a highly pure tetrabromobisphenol-A product by providing a reaction system in which there is directly formed a tetrabromobisphenol-A precipitate at such speed that there is insufficient opportunity for the significant precipitation of the intermediate, tribromobisphenol-A.

As before stated, it is a feature of the processes of this invention, that precipitation of tetrabromobisphenol-A occurs during the feeding of bisphenol-A to the reactor and that the precipitate so formed contains at least 95 wt % tetrabromobisphenol-A and with a yield of at least 90% based on the bisphenol-A fed. This feature is extant whether the process is batch or continuous. When the process is run in the continuous mode, this feature results in the continuous recovery of highly pure tetrabromobisphenol-A from the reaction system. Even further, when the process is run in the batch mode, this feature results in obtaining high purity tetrabromobisphenol-A in the absence of a need for a reaction mass cook time after the last of the reactant feeds has been completed. Indeed, the precipitate can be recovered from the batch reaction mass immediately or as soon as is practical from a materials handling standpoint. The processes of this invention can exhibit yields within the range of from about 90% to about 99.5%, based upon the bisphenol-A fed to the reaction. Preferred yields are within the range of from about 95% to about 99%.

We claim:

1. A process for producing tetrabromobisphenol-A, which process comprises:
   (a) feeding, to a reactor, a solution comprised of bisphenol-A, water and a water miscible solvent to at least partially form a reaction mass having a liquid phase containing from above about 15 to about 65 wt % water, the wt % being based upon the amount of water and water miscible solvent in the liquid phase;
   (b) during (a), feeding a stream of gaseous bromine to the reaction mass, such gaseous feed stream having a Reynold's number $\geq 40\,000$;
   (c) during (a), providing for the presence, in the reaction mass of (i) from about 50 to 20,000 ppm unreacted bromine and (ii) less than about 20 wt % HBr, the ppm and wt % HBr values being based upon the total weight of the liquid phase of the reaction mass; and
   (d) during (a), forming a reaction mass precipitate phase which comprises at least about 96 wt % tetrabromobisphenol-A, the wt % being based on the total weight of the precipitate phase.

2. The process of claim 1 wherein the water miscible solvent is methanol, ethanol or a mixture thereof.

3. The process of claim 2 wherein the water miscible solvent is ethanol.

4. The process of claim 1 wherein the wt % water is within the range of from about 35 to about 65 wt %.

5. The process of claim 2 wherein the methanol or ethanol to bisphenol-A weight ratio in the feed solution is within the range of from about 0.5:1 to about 10:1.

6. The process of claim 1 wherein the Reynold's number is within the range of from about 50,000 to about 1,000,000.

7. The process of claim 1 wherein the amount of unreacted bromine is within the range of from about 1,000 to about 8,000 ppm.

8. The process of claim 1 wherein the amount of unreacted bromine is within the range of from about 2,000 to about 6,000 ppm.

9. The process of claim 1 wherein the liquid phase of the reaction mass contains from about 1 to about 20 wt % HBr, the wt % being based upon the total weight of the liquid phase.

10. The process of claim 9 wherein the liquid phase of the reaction mass contains from about 10 to about 18 wt % HBr.

11. The process of claim 10 wherein the water miscible solvent is ethanol, the wt % water is within the range of from about 35 to about 65 wt %, the ethanol to bisphenol-A weight ratio in the feed solution is within the range of from about 0.7:1 to about 10:1, the Reynold's number is within the range of from about 50,000 to about 1,000,000, the amount of unreacted bromine is within the range of from about 50 to about 15,000 ppm.

12. The process of claim 1 wherein the process is a continuous process.

13. The process of claim 1 wherein HBr in the reaction mass is oxidized to yield bromine.

14. The process of claim 13 wherein the oxidation occurs during (a).

15. The process of claim 13 wherein the oxidant is $H_2O_2$.

16. The process of claim 1 wherein an oxidant is fed to the reaction mass during (a) to oxidize HBr in the reaction mass to yield bromine.

17. The process of claim 16 wherein the oxidant is $H_2O_2$.

18. The process of claim 13 wherein the reaction mass contains from about 1 to about 20 wt % HBr, the wt % being based upon the total weight of the liquid phase.

19. The process of claim 16 wherein the reaction mass contains from about 1 to about 20 wt % HBr, the wt % being based upon the total weight of the liquid phase.

20. The process of claim 18 wherein the reaction mass contains from about 10 to about 15 wt % HBr.

21. The process of claim 20 wherein the water miscible solvent is ethanol, the wt % water is within the range of from about 35 to about 65 wt %, the ethanol to bisphenol-A weight ratio in the feed solution is within the range of from about 0.7:1 to about 10:1, the Reynold's number is within the range of from about 50,000 to about 1,000,000, and the amount of unreacted bromine is within the range of from about 50 to about 15,000 ppm.

22. The process of claim 1 wherein the feed solution is comprised of bisphenol-A, water and a water miscible solvent.

23. The process of claim 22 wherein the water miscible solvent is methanol, ethanol or a mixture thereof.

24. The process of claim 22 wherein wt % water in the feed solution is substantially the same as the wt % water in the reaction mass.

25. The process of claim 22 wherein the Reynold's number is within the range of from about 50,000 to about 1,000,000.

* * * * *

UNITED STATES PATENT AND TRADEMARK OFFICE
CERTIFICATE OF CORRECTION

PATENT NO. : 6,084,136
DATED : July 4, 2000
INVENTOR(S) : Richard A. Holub; Steven R. Alferi; Bonnie G. Mckinnie; Hassan Y. Elnagar It is certified that error appears in the above-indentified patent and that said Letters Patent is hereby corrected as shown below:

Cover Page

Item [73] reads:

"[73]   Assignee:   Albmarle Corporation, Richmond, Va."

and should read:

-- [73]   Assignee:   Albemarle Corporation, Richmond, Va. --.

UNITED STATES PATENT AND TRADEMARK OFFICE
CERTIFICATE OF CORRECTION

PATENT NO. : 6,084,136  
DATED : July 4, 2000  
INVENTOR(S) : Richard A. Holub; Steven R. Alferi; Bonnie G. Mckinnie; Hassan Y. Elnagar Page 2 of 2

It is certified that error appears in the above-indentified patent and that said Letters Patent is hereby corrected as shown below:

Item [63] reads:

"[63]    Continuation-in-part of application No. 08/550,044, Oct. 30, 1995, Pat. No. 5,723,690, application No. 08/426,996, Apr. 24, 1995, abandoned, and application No.08/945,158, Oct. 21, 1997, which is a continuation-in-part of application No. 08/426,998, Apr. 24, 1995, abandoned, which is a continuation-in-part of application No. 08/398,837, Mar. 6, 1995, abandoned, which is a continuation of application No. 08/426,997, Apr. 24, 1995, Pat. No. 5,527,971."

and should read --

-- [63]    Continuation-in-part of application No. 08/945,158, via PCT, Apr. 18, 1996, which is (1) a continuation-in-part of application No. 08/426,998, Apr. 24, 1995, abandoned, which is a continuation-in-part of application No. 08/398,837, Mar. 6, 1995, abandoned; (2) continuation-in-part of application No. 08/550,044, Oct. 30, 1995, Pat. No. 5,723,690, which is a continuation of application No. 08/426,997, Apr. 24, 1995, Pat. No. 5,527,971; and (3) continuation-in-part of application No. 08/426,996, Apr. 24, 19955, abandoned. --.

Column 23, Line 22, reads " ... $\geq$ 40 000;" and should read -- ... $\geq$ 40,000; --.

Signed and Sealed this

Third Day of April, 2001

Attest:

NICHOLAS P. GODICI

*Attesting Officer*        Acting Director of the United States Patent and Trademark Office